US006287259B1

(12) United States Patent
Grunwald

(10) Patent No.: US 6,287,259 B1
(45) Date of Patent: Sep. 11, 2001

(54) SYSTEMS AND METHODS FOR EVALUATING OBJECTS WITHIN AN ULTRASOUND IMAGE

(75) Inventor: Sorin Grunwald, Santa Clara, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/506,513

(22) Filed: Feb. 17, 2000

Related U.S. Application Data

(63) Continuation of application No. 09/165,670, filed on Oct. 2, 1998.

(51) Int. Cl.[7] .................................................... A61B 8/00
(52) U.S. Cl. ........................................... 600/437; 600/467
(58) Field of Search ................................... 600/437, 438, 600/443, 447, 449, 466, 467

(56) References Cited

U.S. PATENT DOCUMENTS

| 4,817,015 | 3/1989 | Insana et al. | 364/507 |
|---|---|---|---|
| 4,855,911 | * 8/1989 | Lele et al. | 600/437 |
| 4,858,124 | 8/1989 | Lizzi et al. | 600/443 |
| 4,982,339 | 1/1991 | Insana et al. | 600/437 |
| 5,417,215 | 5/1995 | Evans et al. | 600/442 |
| 5,782,766 | * 7/1998 | Weng et al. | 600/443 |

FOREIGN PATENT DOCUMENTS

| 2319841 | 6/1998 | (GB) . |
|---|---|---|
| WO 94/23652 | 10/1994 | (WO) . |

OTHER PUBLICATIONS

Frederic L. Lizzi, "New Developments in Ultrasonic Tissue Characterization" *Acoustical Imaging,* vol. 19, H. Ermert & H.P. Harjes, Ed., Plenum Press, New York, 1992.

T. Spencer, M.P. Ramo et al., "Characterisation of Atherosclerotic Plaque by Spectral Analysis of 30 MHZ Intravascular Ultrasound Radio Frequency Data", 1996 IEEE Ultrasonics Symposium.

Athina P. Petropulu, Ray Wang and Katherine Piccoli, "Modeling the Ultrasound Backscattered Signal Using α–Stable Distributions", 1996 IEEE Ultrasonics Symposium.

\* cited by examiner

*Primary Examiner*—Marvin M. Lateef
*Assistant Examiner*—Maulin Patel
(74) *Attorney, Agent, or Firm*—Townsend and Townsend and Crew LLP

(57) ABSTRACT

According to the invention, an object in an ultrasound image is characterized by considering various in-vivo object parameters and their variability within the ultrasonic imaging data. Specifically, it is assumed that the object may be defined in terms of statistical properties (or object identifying parameters), which are consistently different from properties of the environment. Such properties are referred to as the object's signature. The statistical properties are calculated at selected locations within the image to determine if they fall within a predetermined range of values which represents the object. If within the range, the locations are marked to indicate they are positioned within the object. A border may then be drawn around the object and the area calculated.

14 Claims, 6 Drawing Sheets

SYSTEMS AND METHODS FOR EVALUATING OBJECTS WITHIN AN ULTRASOUND IMAGE

This application is a continuation of Ser. No. 09/165,670 filed Oct. 2, 1998.

BACKGROUND OF THE INVENTION

This invention relates to the automated characterization and identification of objects, including automated detection of their borders, in intravascular ultrasonic imaging.

The value of ultrasonic imaging can be enhanced if models can be developed which accurately correlate properties of ultrasound objects in an in-vivo environment. Heretofore there have been few automated approaches in the field of in-vivo ultrasonic object definition and identification. Previously proposed approaches may be classified in two categories. First, the defining of an object as an area surrounded by a detected border. Detection of the border in turn is based on local properties and behavior of the border. Second, the development of a theoretical model for an ultrasound object which is validated for in vitro studies.

According to the first category, approaches have been developed at the Thoraxcenter in Rotterdam, Holland, and at the University of Iowa which employ feature extraction techniques for border detection. In those approaches an object is defined as the area encompassed by a detected border, and the algorithms used are optimized to provide the best possible border. These approaches are limited because algorithms provide little information about the parameters characterizing the object under observation. Neither can the algorithms adapt their behavior in accordance with frame-to-frame variants in object properties. In addition, the algorithms are computational and time intensive in cross-sectional area computation, since they must completely calculate the object border in each frame of the volume.

In the second category of approaches, tissue modeling techniques have been developed for comparing data patterns with predefined models, e.g., at the Stanford Center for Cardiac Interventions and the University of Texas. In these types of techniques, a consistent tissue behavior is assumed which can be modeled. The models describe internal properties of an object which can be used to identify the object. However, such models are inherently limited in that by their nature they cannot accommodate variations in object properties from patient to patient, or even from frame to frame. A paper by Petropulu et al. entitled MODELING THE ULTRASOUND BACKSCATTERED SIGNAL USING $\alpha$-STABLE DISTRIBUTIONS, 1996 IEEE Ultrasonics Symposium, p. 103 is representative of the model-based approach. Therein certain assumptions about theoretical statistical behavior are made, and the assumptions are used to identify the object in an in-vivo case study. This limited approach is subject to significant errors because it yields a model which only partially describes the object behavior and does not take into account variations from case to case.

Most known techniques for object border detection use a purely manual method for border tracing, which is done simply by drawing the boundary of the object. This procedure is slow and is subject to errors and variations between users. Moreover, it does not allow for the characterization of the object within the border.

One known description of a combination of different approaches is Spencer et al., CHARACTERISATION OF ATHEROSCLEROTIC PLAQUE BY SPECTRAL ANALYSIS OF 30 MHZ INTRAVASCULAR ULTRASOUND RADIO FREQUENCY DATA, 1996 IEEE ULTRASONICS SYMPOSIUM, p. 1073, wherein a statistical model is developed from in-vitro studies, then applied to in-vivo cases. Such an approach is limited by both the differences between in-vitro and in-vivo conditions and between in-vivo cases.

What are needed are better techniques for border detection and for identifying and characterizing objects and features of ultrasonic imaging.

SUMMARY OF THE INVENTION

The invention provides exemplary systems and methods for evaluating objects located within ultrasonic images. According to one exemplary method, in-vivo ultrasound image data is obtained and an image is constructed from the data which includes at least one object. At least two parameters are calculated from the data for selected locations within the object. These parameters are representative of the intensity of the object and the spacial structure of the object.

Preferably, the data that is collected is time-domain data. This data is transformed into frequency-domain data and compressed. The two parameters preferably comprise the zero frequency magnitude of the compressed frequency-domain data and the sum of the frequency magnitudes of the compressed frequency-domain data. Use of these two parameters is particularly advantageous in that they may be used to characterize a physical object within a patient. For example, the zero frequency magnitude of the compressed frequency-domain data is representative of the physical composition of the physical object, e.g., its hardness, and the sum of the frequency magnitudes of the compressed frequency-domain data is representative of the structure of the physical object. Hence, the invention provides a way to obtain patient specific parameters in a in-vivo processes. Further, these parameters represent various physical characteristic of the object under evaluation so that a treatment may more carefully be tailored. Moreover, these parameters may be saved and kept as part of the patient's history so that they may be compared to parameters calculated after one or more treatments of the object.

In another exemplary method, in-vivo ultrasound image data is provided in a plurality of frames. An object is identified within each image by moving a region of interest to different locations in the image and evaluating object identifying parameters at the different locations to determine if the parameters fall within an acceptable range that are indicative of the object. The area of the object within each of the frames is then computed based on the area of the locations having the parameters which fall within the acceptable range. The areas of two adjacent frames are then compared to determine if the difference between the two areas exceeds a predetermined amount. If so, the area of one of the adjacent frames is recomputed using different criteria.

For example, the range of acceptable object identifying parameters may be varied when recomputing the area of one of the adjacent frames. As another example, a starting location of the region of interest may be varied when recomputing the area of one of the adjacent frames. As still another example, the size of the region of interest may be varied when recomputing the area of one of the adjacent frames. In the event that the difference between recomputed area and the area of the object in the adjacent frame still exceeds the predetermined amount, a message may be produced indicating the discrepancy.

In one specific embodiment, a method is provided for evaluating an object within an ultrasound image that is constructed from time-domain data. According to the method, a region of interest within the object is selected for observation. At the selected region of interest, a transformation of the time-domain data is performed to obtain frequency-domain data. The frequency-domain data is then compressed or filtered, and object identifying parameters are obtained from the compressed frequency-domain data. Multiple definition regions of interest which are subsets of the selected region of interest are then defined. Preferably, the definition regions of interest are proportional in shape to the selected region of interest and are located at a distinct locations within the selected region of interest. A transformation of the time-domain data defining the definition regions of interest is then performed to obtain frequency-domain data that is representative of the definition regions of interest. From this data, a range of acceptable object identifying parameters is obtained.

Once this range has been determined, definition regions of interest are positioned at selected locations in the ultrasound image, and transformations of the time-domain data are performed to obtain frequency-domain data representative of the definition regions of interest in the ultrasound image. Object identifying parameters from this frequency-domain data are then obtained. These object identifying parameters are then evaluated to determine if they are within the range of acceptable object identifying parameters that was previously calculated. The selected definition regions of interest in the ultrasound image which have object identifying parameters which fall within the acceptable range are then marked or flagged so that an object boundary may be constructed around the flagged definition regions of interest. Once the boundary is constructed, an area of the object may easily be calculated.

In one particular aspect, the data is compressed by evaluating only the data which has a spectral power content below a selected fractional threshold. In another aspect, the object boundary and the object are displayed (such as on a display screen) to allow a user to indicate whether the object boundary acceptably bounds the object. If the constructed boundary is inaccurate or otherwise unacceptable, a new boundary may be constructed in one of two ways. In one way, the user may select another region of interest (e.g., by utilizing a mouse to move the region of interest to another location on the displayed object), and repeating steps of the method with the new region of interest. Alternatively, the data may be compressed or filtered in a different manner, and then repeating the steps of the method.

Typically, the ultrasound image is defined by multiple frames of time-domain data, and the object boundary is constructed in one of the frames (conveniently referred to as a first one of the frames). Another one of the frames is then selected and an object boundary is constructed around the object in the second frame and an area is calculated. This process is repeated for each frame having the object. Hence, one advantage of the invention is that the area of the object in subsequent frames may proceed with essentially no user interaction. Once the areas have been calculated, a volume of the object may be computed based on the areas of the objects in the frames and the distances between the frames.

In one aspect, the object boundary around the object in the second and subsequent frames are constructed by placing a definition region of interest at a center of mass of the object as determined from the first (or a previous) frame and repeating the steps that follow the determination of the range of acceptable object identifying parameters.

In one particularly preferable aspect, the area of the object in the first frame and the second frame are compared to determine if the areas differ by more than a predetermined amount. If so, the area of the object in the second frame is recomputed using varied criteria. For example, the starting point of the definition region of interest in the object of the second frame may be adjusted. Alternatively, the size of the definition region of interest may be changed. Further, the range of acceptable object identifying parameters may be varied.

The invention will be better understood by reference to the following detailed description in connection with the accompanying drawings.

DESCRIPTION OF SPECIFIC EMBODIMENTS

The invention provides exemplary systems and methods for evaluating objects within ultrasonic images. The objects to be evaluated are preferably representative of various physical features within the anatomy. Merely by way of example, such features may include tissue, plaque, blood, and the like.

The invention is particularly useful in constructing a border around the object so that the area of the object may easily be calculated. Importantly, the invention is also useful in that it is able to model the object using parameters which are representative of various physical characteristics of the object. These parameters are obtained from in-vivo image data. As one example, if the physical object is constructed at least partially from plaque, the parameters produced by the invention convey information on the nature of the plaque, e.g. its hardness, homogeneity, and the like. In this way, the parameters may be used to more appropriately define a proscribed treatment. Further, the parameters may be saved so that each time the patient is evaluated, the saved of parameter values may be compared to determine changes over time.

According to the invention, the object is characterized by considering the in-vivo object parameters and their variability within the ultrasonic imaging data. Specifically, it is assumed that each object may be defined in terms of statistical properties (or object identifying parameters), which are consistently different from properties of the environment. Such properties are referred to as the object's signature. The statistical properties are calculated at selected locations within the image to determine if they fall within a predetermined range of values which represents the object. If within the range, the locations are marked to indicate they are positioned within the object. A border may then be drawn around the object and the area calculated.

If the border is not correctly drawn, the method is able to adjust certain criteria and then repeat the process until convergence is obtained. Since the ultrasound data is typically stored in multiple (possibly consecutive) frames, the area of the object in each frame needs to be computed. When computing the area of the object in a subsequent frame, a comparison is made with the previous frame to determine if the variability in the area of the object is too great. If so, the invention allows the user to adjust certain criteria, or else automatically adjusts certain criteria to see if a better result can be obtained. Once the area in each frame is determined, a volume of the object may be computed.

Figure 1:
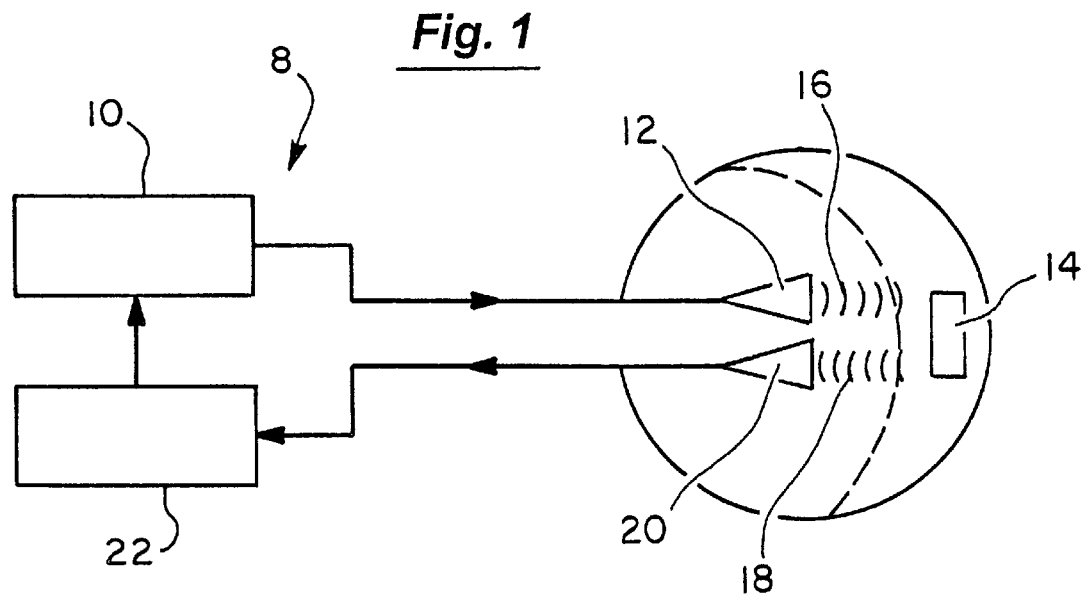
FIG. 1 is a block diagram of an environment of the invention.

Referring now to FIG. 1, an ultrasound system 8 according to the invention will be described. The system 8 includes a transducer 12 (which is typically disposed within an imaging catheter as is known in the art) which is driven by an exciter 10 to excite a region of interest (ROI) 14 with ultrasonic energy 16. Reflections 18 of the ultrasonic energy are observed at a receiver 20 during a frame. Signal processing techniques in a signal processor 22 analyze those reflections. The information extracted is used to refine the excitation and observations about current and/or subsequent frames and to refine the characterization of the frame as an object model. Although not shown, system 8 preferably also includes a display screen to display each frame of data, which is typically a cross section of the image. Various entry devices, such as keyboards, pointing devices, mice, and the like, are preferably provided to allow the user to interact with the system. An exemplary processor that may be used with the invention is included within a Galaxy medical imaging system, commercially available from Boston Scientific Corporation.

Figure 2:
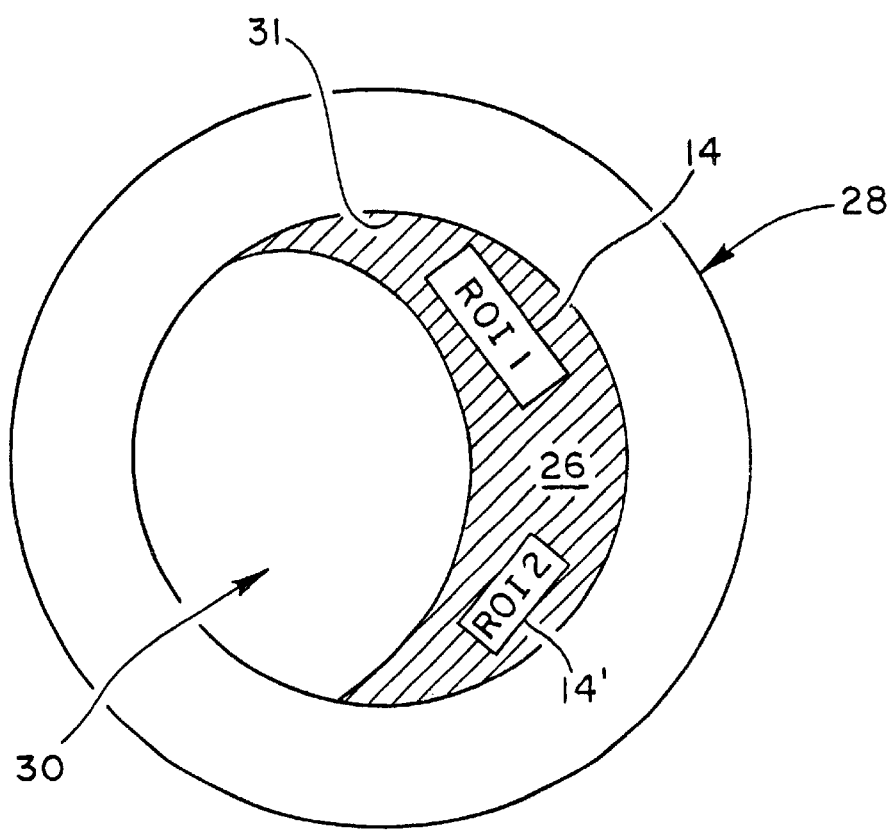
FIG. 2 is a depiction of an in-vivo case showing regions of interest according to the invention.

FIG. 2 illustrates a typical IVUS object 26 (such as plaque) in an image 28 that is produced on the display screen of system 8 and represents a frame of data collected by receiver 20. As described in greater detail hereinafter, drawn onto target object 26 are two different rectangular regions of interest (ROIs) 14, 14'. ROIs 14, 14' may be placed onto object 26 using one of the entry devices of the system as previously described. Moreover, although shown as being rectangular, it will be appreciated that ROIs 14 and 14' may be of any size or geometry. Further, any number of ROIs may be employed.

A lumen 30 surround by a vessel wall 31 illustrates how the plaque 26 fills the lumen 30. As is known in the art, the different objects are characterized by differently displayed visual intensities as well as the homogeneity of the image. As described hereinafter, reflections from ROIs 14, 14' preferably exhibit a spectrum differing from that of any surrounding objects.

Figure 3A:
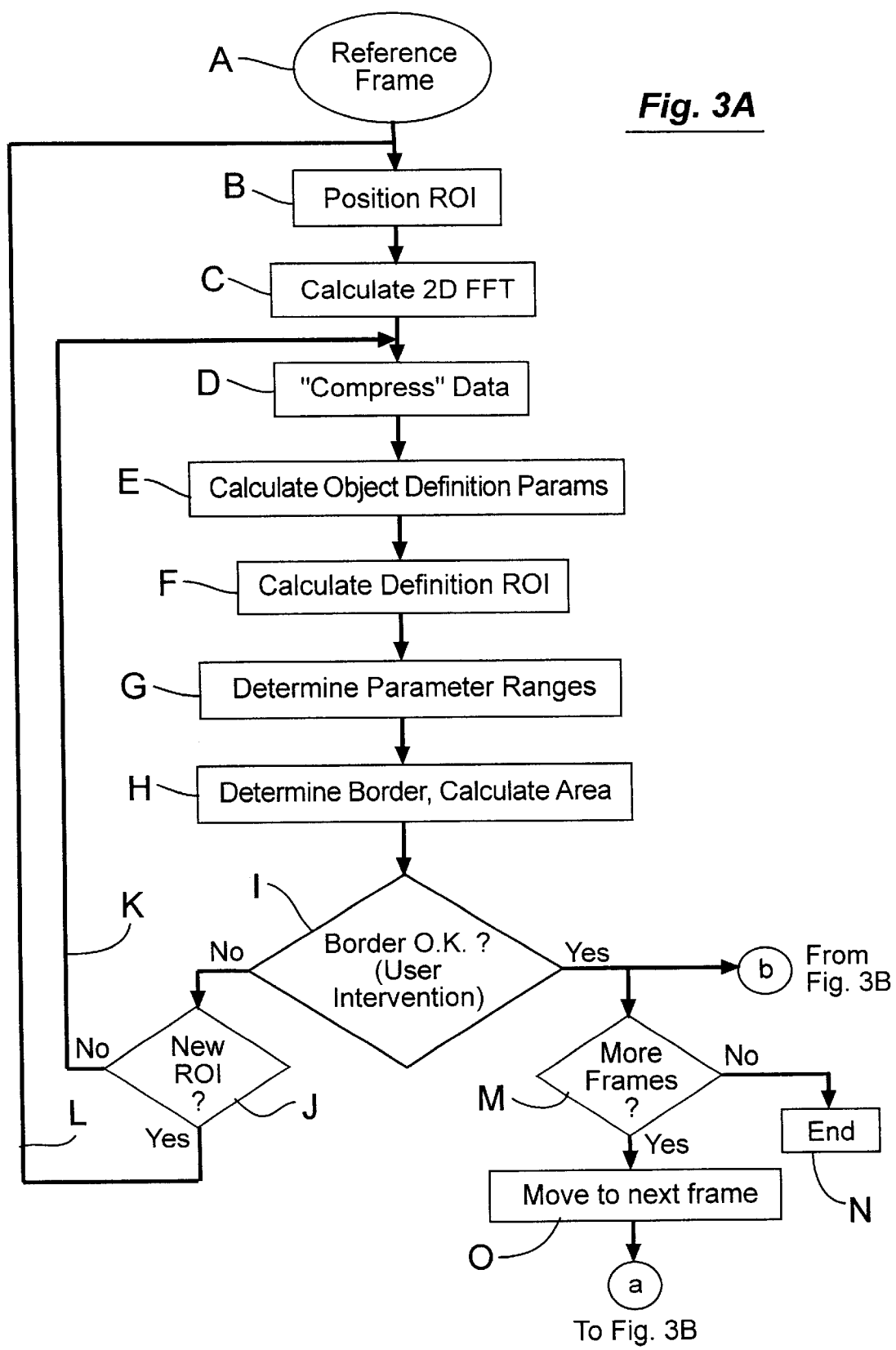
FIGS. 3A and 3B are together a flow chart of a process according to the invention for adaptive computation of an object signature.
Figure 3B:
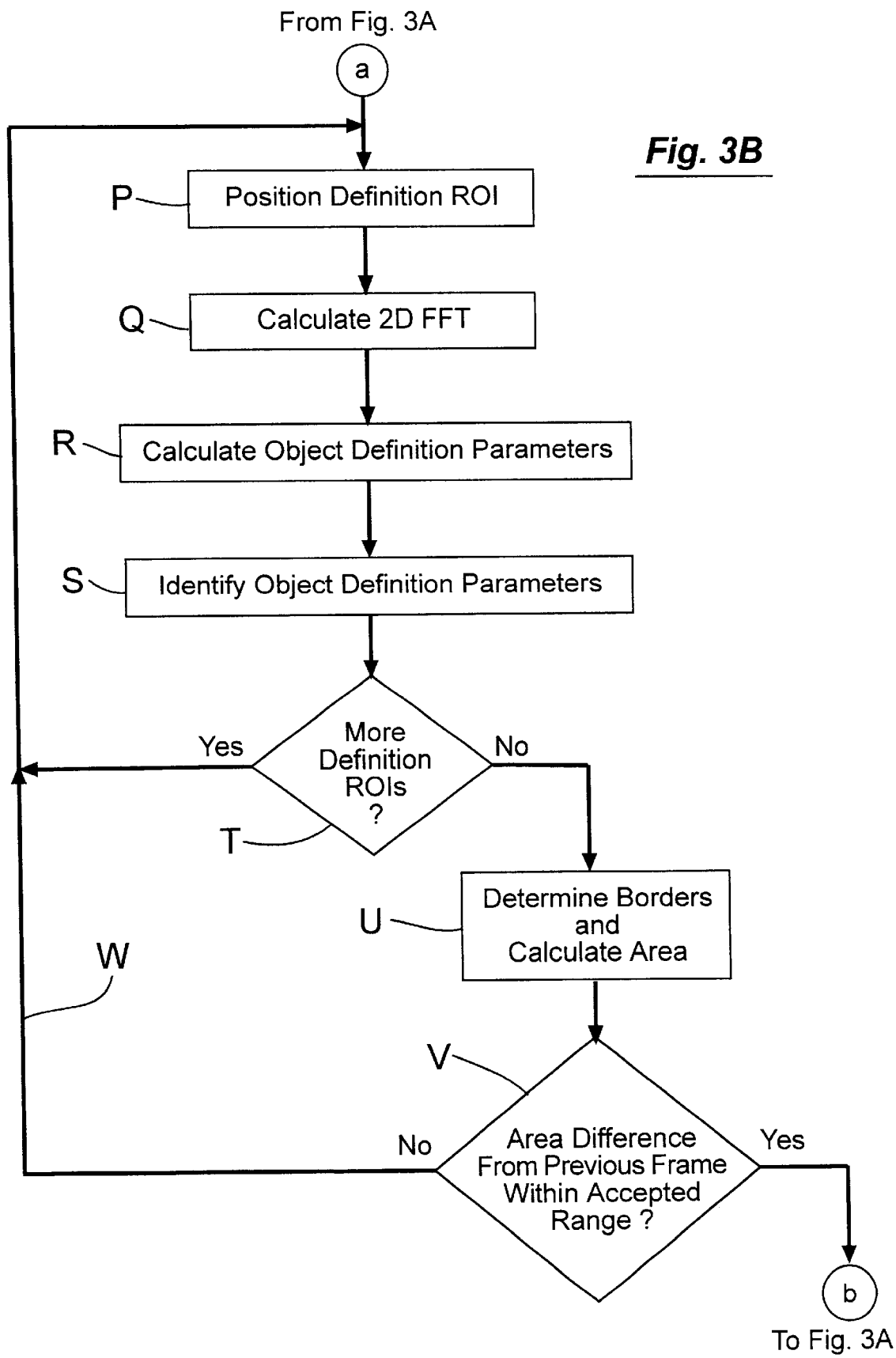

Referring to FIGS. 3A and 3B, a flow chart of an exemplary inventive process is illustrated. The process begins by selecting a reference frame which comprises the observed reflection signal for a time sample of interest (Step A). Preferably, the user is allowed to select the reference frame. The selected frame is preferably the frame which best shows object 26 (see FIG. 2). ROI 14 (see FIG. 2), which may be essentially any size or geometry, is then positioned on the desired object 26 (Step B). This may be accomplished, for example, by using a mouse to outline ROI 14 on the display screen.

Figure 4:
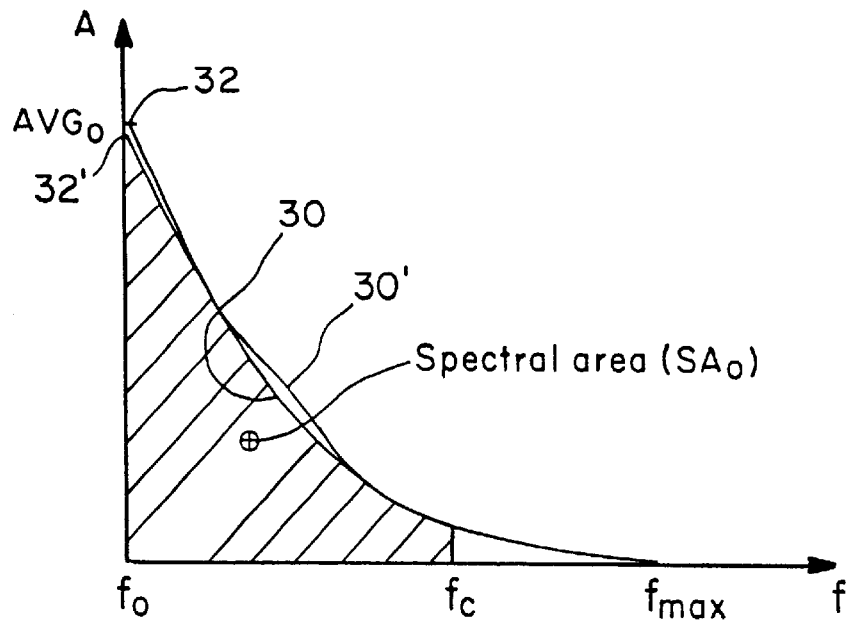
FIG. 4 is a spectrum diagram of a region of interest.

A two-dimensional fast Fourier transform (FFT) is calculated from the observed time-domain data of ROI 14 to obtain frequency-domain data, i.e., a spectrum of the observational data in x and y (Step C). The data is then compressed by retaining only a percentage of the spectral components which represent ROI 14 (Step D). Such a process is illustrated graphically in FIG. 4. As shown in the example of FIG. 4, the spectral components between $f_o$ and $f_c$ are kept. The value $f_c$, i.e. the amount of desired compression, is selected based on a percentage of the original area of the compressed data that is desired to be maintained, e.g., 90% of the area under the curve of FIG. 4. This value may be varied to improve the results of the method as described hereinafter.

Compression of the data may be accomplished, for example, by using a low pass filter. However, it will be appreciated that various other compression schemes may be employed. For example, the method may employ a high pass filter, a band pass filter, a selective filter, and the like. The compressed spectral components are then used to compute two key object identification parameters (Step E). Referring to FIG. 4, these two parameters are the zero frequency magnitude $AVG_o$, i.e., the magnitude of the frequency at $f_0$ (also referred to as the amplitude of zero frequency), and the sum SA of the frequency magnitudes, i.e. the area under the spectral amplitude density curve (also referred to as the spectral amplitude distribution). This area is graphically represented by the cross-hatched area under the curve of FIG. 4. As described hereinafter, these two parameters are particularly advantageous in that they may be used to characterize various physical characteristics of the object within the patient.

Next, a "definition" ROI is calculated. The definition ROI is a subset of the originally selected ROI and is used to obtain a range of acceptable object identification parameters. The definition ROI is preferably selected so that is has a similar geometric shape as the original ROI but with smaller dimensions. Merely by way of example, if the originally selected ROI were a square, and if the number of components from $f_o$ to $f_{max}$ were 256 and the number of components from $f_o$ to $f_c$ were 64 (which is the square root of 256), then the dimensions of the definition ROI may be the square root of 64, or 8 by 8 components. As described hereinafter, the amount of compression can be varied to enhance the results of the method, if needed. Once the dimensions of the definition ROI are determined, the definition ROI is then reconstructed in the time domain from the compressed spectral data (Step F).

The definition ROI is then moved through the originally selected region of interest to unique locations. At each unique location (which may be as close as pixel to pixel) a FFT is performed on the definition ROI and the two object identifying parameters are calculated in a manner similar to the originally selected ROI. These values are then used to determine an acceptable range of object identifying parameters (Step G), since each of the definition parameters belong to the originally observed ROI. This range is illustrated graphically in FIG. 5.

Returning to the original image, the definition ROI is moved to selected locations in the image and FFTs of the time-domain data are performed to obtain frequency-domain data for each location of the definition ROI in the original image. From this data, the two object identification parameters are extracted and evaluated to see if they fall within the range of FIG. 5. If so, the locations are marked or flagged to indicate that these locations are part of the object having the originally selected ROI.

Once all of the locations have been evaluated, a border of the object is "drawn" by the processor around the flagged locations (Step H). The area of the object may easily be calculated simply by summing the areas of the flagged locations.

The user is then presented with the results (by displaying the image with the border on the display screen) and asked to indicate whether the border as presented is correct or otherwise acceptable (Step I). For example, a window may be generated on the display screen to ask the user if the border is acceptable. A confirmation of the border is a confirmation that the object definition is correct. If the border is not confirmed as correct, the user is given the choice (Step J) of optimizing the ROI (Step K) or adding another ROI (such as ROI 14') (Step L). The whole process (Steps B through H) is repeated for each added ROI. A portion of the process. (Steps D through H) is repeated if the ROI is to be optimized. To optimize the ROI, the amount of or type of compression may be varied. Also, the range of acceptable object identifying parameters may be changed.

Figure 6:
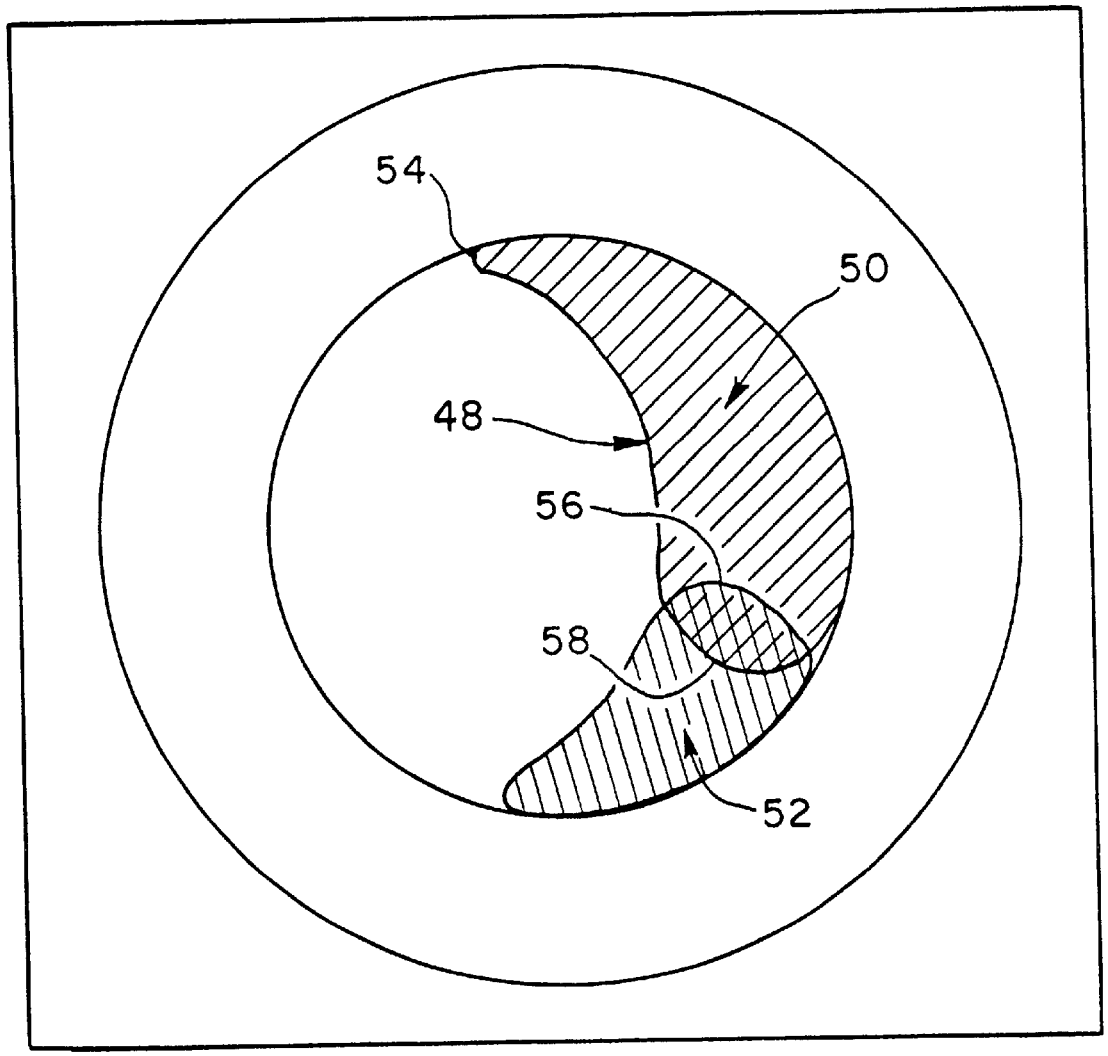
FIG. 6 is a depiction of an object definition according to the invention.

The foregoing process (beginning with Step L) is used for confirming the border of a complex object and thus the definition of a complex object. The complex object is defined by the combined borders of each individual object detected for each individual definition ROI as shown in FIG. 6.

If (in Step I) the border is confirmed, the process proceeds to the next frame, first determining if there are more frames (Step M). If there are no more frames, the process ends (Step N). If there are still more frames, the process proceeds to the next frame (Step O).

Referring to FIG. 3B, processing on subsequent frames proceeds with positioning of a definition ROI (which is preferably the same definition ROI previously calculated) at a center of mass of the object (which is approximated from the object in this previous frame) (Step P). A two-dimensional fast Fourier transform (FFT) is then calculated on the time-domain data (Step Q) in order to calculate object definition parameters (step R) and then identify the object definition parameters (step S), using the same techniques used previously. The parameters are examined to determine if they are within the acceptable range as previously calculated. If so, the location of the definition ROI is flagged as defining an area belonging to the object. So long as there is an unprocessed definition ROI (Step T), the process of Steps P through S repeats for all definition ROIs. After all definition ROIs have been considered, the borders of the final object are determined and the area contained therein is calculated (Step U) in a manner similar to that previously described.

The new area value is compared with the area value computed for the previous frame to determine whether it is within an acceptable range (Step V). If it is, the process proceeds to the next frame (Step M, FIG. 3A). If not, the process enters an adaptive loop (Step W) repeating steps P through U) with a change of position and size of the definition ROIs or a change in the range of acceptable parameters in order to obtain an area value within an acceptable range.

If the two compared areas are substantially different from each other, there is a strong likelihood that one of the areas has been incorrectly computed. The loop of steps P through U provides an adaptive way to compensate for such discrepancies. More specifically, the value of $f_c$ (see FIG. 2) may be varied (or the data may be compressed in any way). Further, the starting point of the definition ROI may be moved away from the center of mass. Still further, the range of acceptable object identification parameters may be varied. In the event that convergence is not obtained, the system may produce a message indicating that the results did not comply with the definition.

FIG. 4 is a spectrum diagram of one ROI 14 from the average frequency $f_0$ to a frequency beyond the maximum observed frequency $f_{max}$. A value $f_c$ denotes the upper limit of the spectrum of the compressed values. As previously explained, the two parameters used to develop an object definition are 1) the zero frequency magnitude AVG, i.e., the amplitude at $f_0$, and 2) the spectral area SA, namely, the area bordered by the axes, the compression cutoff and the amplitude-frequency plot 30. This plot differs with each definition ROI, as represented by plot 30', just as the zero frequency magnitude AVG differs between amplitude 32 and 32'.

Figure 5:
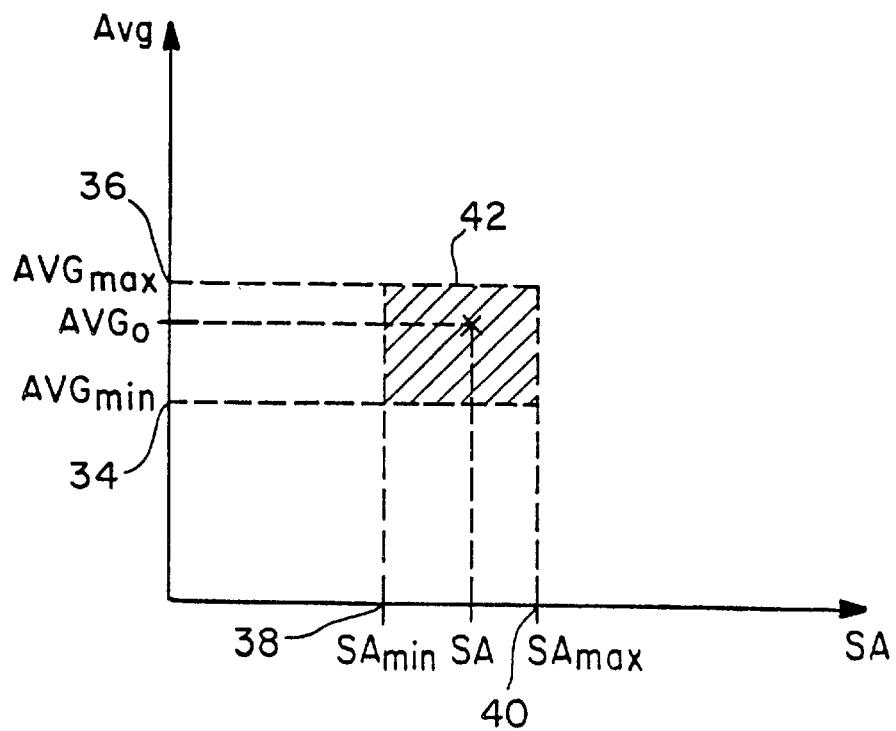
FIG. 5 is a graph of variation in an object range.

FIG. 5 depicts a relationship between spectral areas SA and zero frequency magnitudes AVG, and more particularly shows the object definition range as computed in Step G (FIG. 3A). Within an object, the parameter AVG may vary between a minimum 34 and a maximum 36, and the parameter SA may vary between a minimum 38 and a maximum 40 thus establishing the allowable parameter variations 42 for the definition of the object's signature. Parameters found within this range are thus identifiable with the object.

Referring to FIG. 6, the object definition algorithm, as outlined in connection with FIG. 3A and FIG. 3B, produces an object definition 48, e.g., for plaque, which for purposes of illustration consists of two objects 50 and 52. An object border 54 combines borders 56, 58 resulting from processing of two ROIs defining the object.

The object area is thereafter useable as a feedback parameter for the adaptive object identification algorithm as disclosed herein. The object identification algorithm in frames other than the reference frame (Step A) uses the results of thee previous frame to identify the object. If the object area in such a frame differs more than an accepted fraction from the previous frame, then the adaptive mechanisms change the positions and sizes of definition ROIs until the resultant new area is within an accepted fraction of the area in the previous frame. If there is no solution to the optimization process (i.e., the solution does not converge), then a best available approximation may be chosen as the solution, and the border area may be denoted as uncertain.

Figure 7:
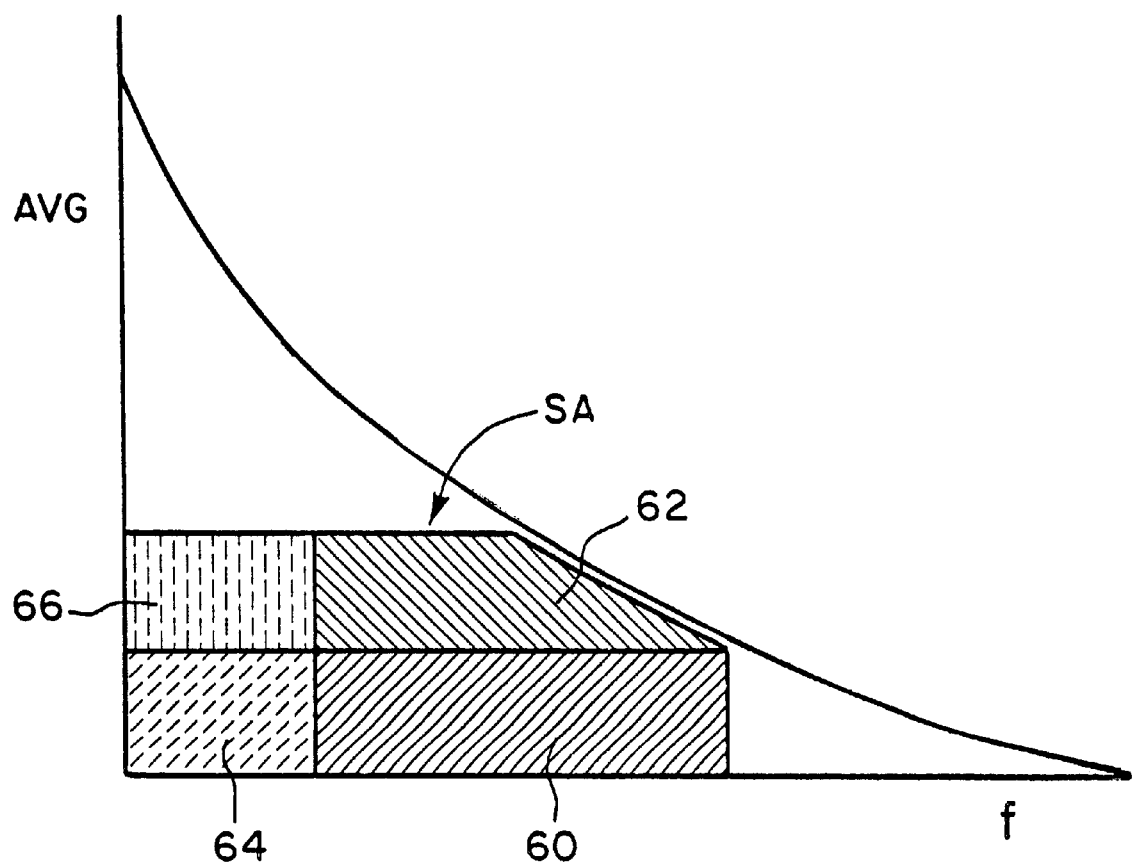
FIG. 7 is a spectrum diagram of a region of interest showing how the object identification parameters are representative of physical characteristics of the object within a patient.

Referring now to FIG. 7, an example of a spectrum diagram of a region of interest showing how the object identification parameters relate to the physical characteristics of the object, i.e. the object within the patient. In this example, the ultrasound image is taken within a vessel having a region of plaque. The AVG axis is representative of the intensity of the ultrasound image. In turn, this corresponds to the physical composition of the actual physical image, e.g., its hardness. The f axis is representative of the spacial structure of the ultrasound image. In turn, this corresponds to the spacial structure, e.g. homogeneity, of the physical object. By way of example, in region 60, the actual physical object is composed of lipid plaque. In region 62, the physical object is composed of mixed plaque. In region 64, the physical object is composed of blood, and in region 66 the physical object is composed of strong calcified plaque that is transitioning into tissue.

Hence, by using the $f_o$ and SA values as object identification parameters, the actual physical nature of the object may be characterized. In this way, the methods of the invention are patient specific and will vary from patient to patient. Moreover, the parameters may be saved and compared with later calculated parameters to determine if a treatment is effective.

The invention has been explained with reference to specific embodiments. Other embodiments will be apparent to those of ordinary skill in the art. It is therefore not intended that this invention be limited except as indicated by the appended claims.

What is claimed is:

1. A method for evaluating an object within an ultrasound image, the method comprising:

obtaining in-vivo ultrasound image data indicative of an object and the environment surrounding the object;

constructing an image from the data, wherein the image includes a depiction of the object and the surrounding environment;

calculating statistical properties from the data at locations within the image;

determining whether the statistical properties are within a certain range that is representative of the object; and constructing a border around the object depicted in the image based at least in part on the determination.

2. A method as in claim 1, wherein the data is time-domain data, further comprising transforming the time-domain data into frequency-domain data and compressing the frequency-domain data, and wherein the statistical properties include parameters that comprise the zero frequency magnitude of the compressed frequency-domain data and the sum of the frequency magnitudes of the compressed frequency-domain data.

3. A method as in claim 2, wherein the object is representative of a physical object within a patient, and wherein the zero frequency magnitude of the compressed frequency-domain data is representative of the physical composition of the physical object, and the sum of the frequency magnitudes of the compressed frequency-domain data is representative of the homogeneity of the physical object.

4. A method as in claim 2, further comprising introducing a catheter into a patient an actuating an ultrasonic element to obtain the time-domain data.

5. A method for evaluating an object within the ultrasound image, the method comprising:

obtaining in-vivo ultrasound image data in a plurality of frames;

constructing images from at least some of the frames of data, wherein the images include at least one object;

identifying the object within each image by moving a region of interest to different locations in the image and evaluating object identifying parameters at the different locations to determine if the parameters fall within an acceptable range of object identifying parameters indicative of the object; and computing the area of the object within each of the frames based on the locations having the parameters which fall within the acceptable range.

6. A method as in claim 5, further comprising comparing the areas of two adjacent frames, recomputing the area of one of the adjacent frames using different criteria if the difference between the two areas exceeds a predetermined amount, and varying the range of object identifying parameters to recompute the area of one of the adjacent frames.

7. A method as in claim 5, further comprising varying a starting location of the region of interest to recompute the area of one of the adjacent frames.

8. A method as in claim 5, further comprising varying the size of the region of interest to recompute the area of one of the adjacent frames.

9. A method as in claim 6, further comprising producing a message if the difference between recomputed area and the area of the object in the adjacent frame still exceeds the predetermined amount.

10. An ultrasound imaging system comprising:

a processor;

a memory to store in-vivo ultrasound image data;

a display screen coupled to the processor;

code to display an image from the data on the display screen, wherein the image includes at least one object;

code to calculate with the processor statistical properties from the data at locations within the image and to determine whether the statistical properties are within a certain range that is representative of the object; and code to construct an object boundary around the object.

11. A system as in claim 10, wherein the data is time-domain data, further comprising code to transform with the processor the time-domain data into frequency-domain data and to compress the frequency-domain data, and wherein the statistical properties include parameters that comprise the zero frequency magnitude of the compressed frequency-domain data and the sum of the frequency magnitudes of the compressed frequency-domain data.

12. A system as in claim 11, wherein the object is representative of a physical object within a patient, and wherein the zero frequency magnitude of the compressed frequency-domain data is representative of the physical structure of the physical object, and the sum of the frequency magnitudes of the compressed frequency-domain data is representative of the homogeneity of the physical object.

13. A system as in claim 11, further comprising a catheter having an ultrasonic element which is coupled to the processor to obtain the time-domain data when the catheter is inserted into a patient.

14. An ultrasound imaging system comprising:

a processor;

a memory to store in-vivo ultrasound image data in a plurality of frames;

a display screen coupled to the processor;

code to display images from each frame of data on the display screen, wherein the images include at least one object;

code to identify the object within each image by moving a region of interest to different locations in the image and evaluating object identifying parameters at the different locations to determine if the parameters fall within an acceptable range of object identifying parameters indicative of the object;

code to compute the area of the object within each of the frames based on the locations having the parameters which fall within the acceptable range;

code to compare the areas of two adjacent frames; and code to recompute the area of one of the adjacent frames using different criteria if the difference between the two areas exceeds a predetermined amount.

* * * * *